United States Patent [19]

Heywang et al.

[11] Patent Number: 5,008,430
[45] Date of Patent: Apr. 16, 1991

[54] MERCAPTOPYRENES, PREPARATION THEREOF AND USE THEREOF FOR THE PREPARATION OF CHARGE TRANSFER COMPLEXES

[75] Inventors: Gerhard Heywang, Bergisch Gladbach; Friedrich Jonas, Aachen, both of Fed. Rep. of Germany

[73] Assignee: Bayer Aktiengesellschaft, Leverkusen, Fed. Rep. of Germany

[21] Appl. No.: 335,902

[22] Filed: Apr. 10, 1989

[30] Foreign Application Priority Data

Apr. 29, 1988 [DE] Fed. Rep. of Germany ....... 3814534

[51] Int. Cl.$^5$ .......................................... C07C 321/28
[52] U.S. Cl. .................... 558/396; 562/427; 564/341; 568/44; 568/47; 568/48; 568/49; 568/56; 568/57
[58] Field of Search ............. 568/57, 56, 47, 48, 568/49, 44; 558/396; 562/427; 564/341

[56] References Cited

U.S. PATENT DOCUMENTS

| | | | |
|---|---|---|---|
| 3,576,882 | 4/1971 | Clark | 568/57 |
| 4,287,125 | 9/1981 | Soula | 568/55 |
| 4,631,143 | 12/1986 | Praefcke et al. | 568/58 |

FOREIGN PATENT DOCUMENTS 279860  12/1964  Australia ............................ 568/58

OTHER PUBLICATIONS

Hackh's Chemical Dictionary, Fourth Edition, p. 16 (1972), McGraw-Hill, Inc., N.Y.
Electronic Conduction in Complexes of Aromatic Hydrocarbons with Iodine, J. Kommandeur, the Journal of Chemical Physics, vol. 34, No. 1, Jan. 1961, pp. 129–133.
Radikalkationensalze einfacher Areneeine neue Familie, organischer Metalle Angew. Chem. 92 (1980), Nr. 11 Verlag Chemie. GmbH D–6940 Weinheim, 1980, pp. 941–942.
Oxidation, Reduction, and Electrochemiluminescence of Donor-Substitued Polycyclic Aiomatic Hydrocarbons, Arnold Zweig, Maurer and Roberts, vol. 32, May 1967, pp. 1322–1329, Journal Org. Chem.

*Primary Examiner*—Mary E. Ceperley
*Attorney, Agent, or Firm*—Sprung Horn Kramer & Woods

[57] ABSTRACT

The invention relates to mercaptopyrenes of the formula

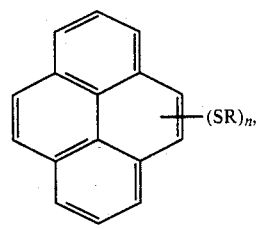

(I)

in which
  n denotes a whole number from 3 to 10 and
  R stands for a substitute or unsubstituted alkyl, alkenyl, alkynyl, cycloalkyl, aralkyl or aryl radical to a process for its preparation, its use for the preparation of CT complexes and to the CT complexes obtained.

1 Claim, No Drawings

MERCAPTOPYRENES, PREPARATION THEREOF AND USE THEREOF FOR THE PREPARATION OF CHARGE TRANSFER COMPLEXES

The invention relates to novel mercaptopyrenes, preparation thereof and the use thereof for the preparation of electrically conducting salts (charge transfer complexes) of mercaptopyrenes. (The charge transfer complexes are hereinafter abbreviated as CT complexes). The invention further relates to CT complexes of mercaptopyrenes.

It is already known that pyrene forms electrically conducting radical cation salts in anodic oxidation in the presence of suitable anions (see Angew. Chem. 92, 941 (1980)) and forms electrically conducting pyrene/iodine complexes upon heating with iodine (see J. Chem. Physics 34, 129 (1961)). However, these conducting pyrene compounds have the disadvantage of not being stable and instead losing their conductivity upon storage in air. It is furthermore known that in solutions of di(methylmercapto)pyrene unstable radical cations are formed in successive electrochemical reductions and oxidations (cyclic voltammetry) (see J. Org. Chem. 32, 1322 (1967)).

It has now been found that mercaptopyrenes which contain three and more mercapto groups in the pyrene molecule can be oxidized to salts (CT complexes) in a simple manner and that these CT complexes have very good electrical conductivity, high stability and good processing properties. Compared to the hitherto known CT complexes of tetracyanoquinodimethane (TCNQ), of tetrathiafulvalene and bis(ethyleneodithio)tetrathiafulvalene, the CT complexes obtainable from the mercaptopyrenes according to the invention represent a novel interesting alternative because of their easier availability, higher stability and improved processability.

The invention accordingly relates to mercaptopyrenes of the formula

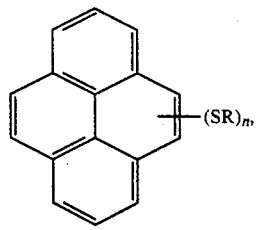

(I)

in which
- n denotes a whole number from 3 to 10, preferably 3 or 4 and
- R stands for a substituted or unsubstituted alkyl, alkenyl, alkinyl, cycloalkyl, aralkyl or aryl radical, preferably for a $C_1$–$C_{12}$-alkyl radical.

Examples of suitable Rs are: as substituted or unsubstituted alkyl radicals $C_1$–$C_{22}$-alkyl radicals such as methyl, ethyl, n- and i-propyl, n-, sec.- and tert.-butyl, 2-ethylhexyl, n-dodecyl, palmityl, stearyl and behenyl radical and $C_1$–$C_{12}$alkyl radicals substituted by halogen, hydroxyl, $C_1$–$C_4$alkoxy, nitro, cyano, carboxyl, $C_1$–$C_4$-alkoxycarbonylacyl or amino such as the 2-chloro, 2-bromo, 2-hydroxy, 2-methoxy, 2-cyanoethyl radical, trifluoroethyl, trichloromethyl, carboxymethyl, ethoxycarbonylmethyl and benzoylmethyl radical;
- as substituted or unsubstituted alkenyl radicals in particular the allyl and oleyl radical;
- as substituted or unsubstituted alkinyl radical the propargyl radical;
- as substituted or unsubstituted cycloalkyl radicals in particular the cyclohexyl radical and cyclohexyl radical substituted by $C_1$–$C_4$-alkyl or halogen such as the methyl- and dimethylcyclohexyl, tert.-butyl- and chlorocyclohexyl radical;
- as aralkyl radicals preferably the benzyl and 2-phenylethyl radical and benzyl radical substituted by $C_1$–$C_4$-alkyl, $C_1$–$C_4$-alkoxy or halogen such as the 4-methylbenzyl, 3-chlorobenzyl and the 4-methoxybenzyl radical; as substituted or unsubstituted aryl radicals in particular the phenyl radical and phenyl radicals substituted by $C_1$–$C_4$-alkyl, $C_1$–$C_4$-alkoxy or halogen such as phenyl, tolyl, xylyl, 4-methoxyphenyl and 2,4-dichlorophenyl radical.

Preferred examples of R are $C_1$–$C_{22}$-alkyl, benzyl and phenyl radicals which are unsubstituted or substituted by $C_1$–$C_4$-alkyl, $C_1$–$C_4$-alkoxy and/or halogen.

Examples of suitable mercaptopyrenes according to the invention of the formula I are in particular: 1,3,6-trimethylmercaptopyrene, 1,3,6,8-tetramethylmercaptopyrene, 1,3,6,8-tetraethylmercaptopyrene, 1,3,6,8-tetra-isopropylmercaptopyrene, 1,3,6,8-tetrabutylmercaptopyrene, 1,3,6,8-tetrahexylmercaptopyrene, 1,3,6,8-tetraoctylmercaptopyrene, 1,3,6,8-tetradodecylmercaptopyrene, 1,3,6,8-tetrabenzylmercaptopyrene, 1,3,6,8-tetraphenylmercaptopyrene.

The mercaptopyrenes according to the invention of the formula I are obtained by reaction of halopyrenes of the formula

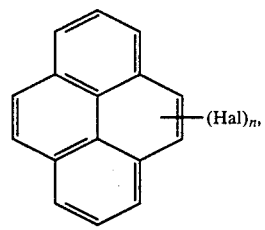

(II)

in which
- n has the meaning mentioned in formula (I) and
- Hal stands for halogen, preferably for chlorine or bromine, with mercaptides of the formula $$K^{m\oplus}(SR)_m \qquad (III),$$

in which
- R has the meaning mentioned in formula (I) and
- $K^{m\oplus}$ stands for an m-valent cation, preferably an alkali metal or alkaline earth metal ion, in a strongly polar, aprotic organic solvent at temperatures of 0° to 150° C., preferably 20° to 150 C.

The invention therefore also relates to a process for the preparation of mercaptopyrenes of the formula I, which is characterized in that halopyrenes of the formula II are reacted with mercaptides of the formula III in a strongly polar, aprotic organic solvent at temperatures of 0° to 150° C., preferably 20° to 150° C.

The halopyrenes of the formula II and their preparation are known (see, for example, DE-OS (German Published Specification) 3,532,882 and Liebigs Ann. Chem. 531, 2 ff (1937).

The mercaptides of the formula III can be used as such or, alternatively, be generated in situ in the reaction mixture from the corresponding mercaptans and bases, for example sodium hydride or sodium methylate.

Examples of strongly polar, aprotic solvents are in particular dimethylformamide, dimenthylacetamide, N-methylpyrrolidone, N-methylcaproplactam, tetramethylene sulphone, ethylene carbonate, propylene carbonate, N,N'-dimethylimidazolidinone and tetramethylurea.

The mercaptopyrenes according to the invention of the formula I can be oxidized to electrically conducting salts (CT complexes) chemically or electrochemically; the composition of these CT complexes can be described by the formula

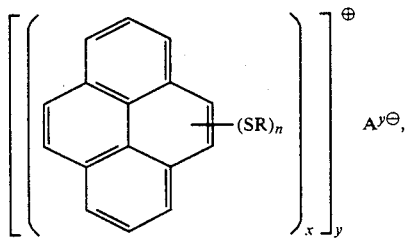

in which
R and n have the meaning given in formula I,
x indicates the total number of the neutral and charged mercaptopyrene units contained in a monovalent mercaptopyrene cation and is a whole or fractional number from 1 to 10, preferably 1 to 5, $A^\ominus$ stands for an anion and
y denotes the number of negative charges (that is, the negative valents) of the anion and the number of monovalent mercaptopyrene cations necessary to neutralize these negative charges and is a whole number from 1 to 3, preferably 1.

Suitable anions are monovalent anions such as $CL^\ominus$, $Br^\ominus$, $I^\ominus$, $I_3^\ominus$, $HSO_4^\ominus$, the methosulfate, tosylate, perchlorate, tetrafluoroborate or hexafluorophosphate ion, but also divalent ions such as the sulphate and trivalent ions such as the phosphate ion are suitable. Preference is given to monovalent anions such as the methosulphate, hexafluorophosphate, tetrafluoroborate, perchlorate, $J_3^\ominus-$, $Br_3^\ominus-$ and the tosylate anion.

The oxidation of the mercaptopyrenes according to the invention can be carried out both electrochemically and also chemically. The electrochemical oxidation is carried out in inert solvents in the presence of conducting salts.

The inert solvents used are preferably: nitriles such as acetonitrile, propionitrile and butyronitrile; amides such as dimethylformamide and dimethylacetamide, ureas such as tetramethylurea, carbonates such as 1,3-dioxa-2-cyclohexanone and 1,3-dioxa-4-methyl-2-cyclopentanone; lactones and lactams such as butyrolactone and N-methylpyrrolidone and caprolactam; sulphoxides and sulphones such as dimethyl sulphoxide and dimethyl sulphone and tetramethylene sulphone; aromatic hydrocarbons such as toluene, xylene and chlorobenzene, ketones such as acetone or cyclohexanone; alcohols such as methanol and ethanol; halogenated hydrocarbons such as methylene chloride and 1,2-dichloroethane. Even water and inorganic solvents such as liquid sulphur dioxide can be used.

Suitable conducting salts are the fluorides, chlorides, bromides, iodides, monoalkylsulphates, perchlorates, tetrafluoroborates, hexafluorophosphates, hexafluoroantimonates, hexafluoroarsenates, methanesulphonates, trifluorumethanesulphonates, benzenesulphonates, tosylates, benzoates and acetates of alkali and alkaline earth metals or of copper and silver, further of onium compounds which have been obtained by exhaustive alkylation of arsines, phosphines, thioethers or tertiary amines. These onium salts can be directly used in the form in which are formed in the exhaustive alkylation. However, it is also possible first to exchange their anion for another anion, for example in tetrabutylammonium chloride, the chloride ion for the tetrafluoroborate ion.

Electrochemical oxidation is carried out at temperatures of $-78°$ C. to the boiling point of the solvent used. Temperatures of $0°$ to $100°$ C., in particular of $20°$ to $85°$ C., are preferred.

The concentrations of the mercaptopyrenes in the solutions to be electrolyzed are between 0.001 mol/l and the saturation concentration of the mercaptopyrene in question in the particular solvent at the temperature used. Concentrations of 0.005 to 0.02 mol of mercaptopyrene per liter of solution are preferred.

The conducting salts can be used in a two- to twentyfold molar excess, relative to the mercaptopyrene used. 3 to 12 mol of conducting salt per mole of mercaptopyrene are preferably used.

The electrochemical oxidation can be carried out potentiostatically or galvanostatically. The galvanostatic operation is preferred. In a typical galvanostatic experiment, electrolysis is carried out in a 100 ml cell, in which two 16 $cm^2$ Pt electrodes are arranged at a distance of 1 cm, at a current of 1.5 mA and a cell voltage between 0.7 and 5 V. If appropriate, anode and cathode space can also be separated by a membrane or a fritted partition.

The CT complexes of the mercaptopyrenes according to the invention are deposited during the electrolysis on the anode and are recovered analytically pure in a known manner by mechanical removal, washing with one of the abovementioned inert solvents and drying.

In the chemical oxidation, the mercaptopyrenes according to the invention are reacted with conventional oxidizing agents. The amount of oxidizing agent is thus that 0.1 to 5 equivalents of oxidizing agent are used for 1 mole of mercaptopyrene. By choosing the amount of oxidizing agent, it is possible to influence the number "x", which influences the total number of mercaptopyrene units contained in the monovalent mercaptopyrene cation. The smaller the amount of oxidizing agent, the higher the number of neutral mercaptopyrene units in the mercaptopyrene cation.

The oxidation of the mercaptopyrenes according to the invention is carried out in the presence of liquid diluents. The mercaptopyrenes can be completely or partly dissolved in this liquid medium or, alternatively, only be present as a suspension.

Suitable oxidizing agents for the oxidation of the mercaptopyrenes according to the invention of the formula I are not only those usually used for chemical oxidation of chemical compounds, such as $H_2O_2$, Caro's acid, perborates, peroxydisulphates, perbenzoic acid, ozone, halogens such as chlorine, bromine or or iodine, potassium permanganate, potassium chromate, potassium dichromate; oxidizing agents such as iron(III) salts such as FE(III) chloride, Fe(III) tosylate, Fe(III) perchlorate, Fe(III) 4-dodecylbenzenesulphonate, furthermore nitronium hexafluorophosphate, nitronium hexafluoroarsenate, nitronium hexafluoroantimonate, nitronium tetrafluoroborate, nitrosonium hexafluorophosphate, nitrosonium hexafluoroarsenate, nitrosonium hexafluoroantimonate, nitrosonium tetrafluoroborate, which are used for the oxidative polymerization of heterocyclic compounds to give electrically conducting polymers; and oxidizing agents such as arsenic pentafluoride, antimony pentafluoride, arsenic pentachloride, antimony pentachloride, aluminium chloride, tin tetrachloride and tin tetraiodide, which are used for the oxidative doping (p-doping) of polyacetylenes and polysulphides to give electrically conducting polyacetylenes and polysulphides.

The diluents used are preferably organic solvents which are capable of readily dissolving the mercaptopyrenes.

In the presence of further salts or acids in the reaction solution, it is possible to incorporate the anions thereof formed by dissociation into the CT complexes of the mercapto-substituted pyrenes.

The chemical oxidation is carried out at temperatures of 0° to 200° C., preferably in the range from 0° C. to the boiling point of the solvent used, if necessary even under pressure.

The CT complexes obtainable by oxidation of the mercaptopyrenes according to the invention are useful organic electrically conducting compounds. They are suitable for the antistatic finish of plastics and as organic conductors in electronics for transmitting electric signals and electrical energy.

The electric conductivities [S/cm] given for the CT complexes in the examples which follow were determined by the 4-electrode-method using pellets, unless stated otherwise.

EXAMPLE 1

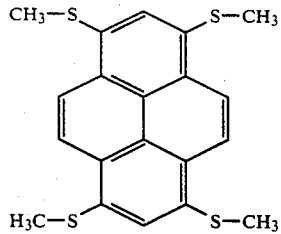

(a) 19.2 g (0.4 mol) of methyl mercaptan are slowly passed at 0° C. with stirring into the suspension of 12 g (0.4 mol) of sodium hydride (80% strength in paraffin) in 200 ml of 1,3-dimethyl-2-imidazolidinone, which is present in a 2000 ml three-neck flask equipped with a stirrer, gas inlet tube and reflux condenser. 25 g (0.05 mole) of 1,3,6,8-tetrabromopyrene are then introduced into the suspension of sodium methyl mercaptide with stirring. The reaction mixture is stirred for 1 hour at room temperature, then for 24 hours at 40° C. The yellow precipitate is then filtered off with suction, washed with water and methanol and dried for 1 hour at 100° C. in vacuo.

This gives 18.9 g (98% of theory) of 1,3,6,8-tetramethylmercaptopyrene in the form of a yellow powder. M.p.: 275°-280° C. (sintering above 250° C.).

(b) (9.6 g (0.2 mol) of methyl mercaptan are slowly passed at 0° C. with stirring into the solution of 10.8 g (0.2 mol) of sodium methylate in 100 ml of dimethylformamide present in a 500 ml three-neck flask equipped with a stirrer, gas inlet tube and reflux condenser. 12.5 g (0.025 mol) of 1,3,6,8-tetrabromopyrene are added with stirring to the suspension of sodium methyl mercaptide in dimethylformamide obtained in this manner. The reaction mixture is stirred for 1 hour at room temperature and 24 hours at 40° C. The yellow precipitate is then filtered off with suction, washed with water and methanol and dried for 1 hour at 100° C. in vacuo.

This gives 9.6 g (=99.5% of theory) of 1,3,6,8-tetramethylmercaptopyrene in the form of a yellow powder. M.p.: 275°-280° C., (sintering above 250° C.).

(c) By passing methyl mercaptan into the solution of sodium methylate in methanol, sodium methyl mercaptide is obtained after the removal of the solvent and drying of the residue in the form of a colourless, fine, free-flowing powder.

29 g (0.41 mol) of this sodium methyl mercaptide are dissolved in 800 ml of dimethylformamide. 46.6 g (0.09 mol) of 1,3,6,8-tetrabromopyrene are added to the solution. The solution readily turns deep yellow. The reaction mixture is stirred for 15 hours at 100° C., and 800 ml of water are then added. The precipitate is filtered off, washed with methanol and water and dried in a This gives 31.5 g (=91% of theory) of 1,3,6,8-tetramethylmercaptopyrene in the form of a yellow powder. M.p.: 275°-280° C (sintering above 250° C.).

EXAMPLE 2

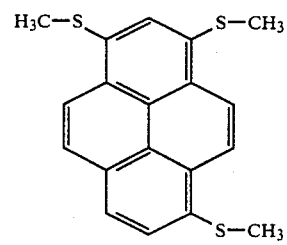

11 g (0.15 mol) of sodium methyl mercaptide are reacted with 22 g (0.05 mol) of 1,3,6-tribromopyrene in 150 ml of N,N'-dimethyl-2-imidazolidinone in the manner described in Example 1 c).

This gives 15.1 g (=88% of theory) of 1,3,6-trimethylmercaptopyrene in the form of a yellow powder; m.p.: 235°-240° C.

EXAMPLE 3

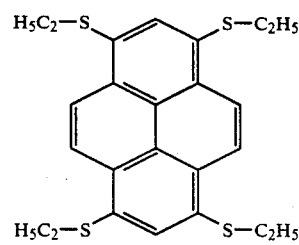

In the reaction vessel described in Example 1 a), 24.8 g (0.4 mole) of ethyl mercaptan are slowly added at 0° C. to the suspension of 12 g (0.4 mol) of sodium hydride (80% strength in paraffin in 100 ml of 1,3-dimethyl-2-imidazolidinone. 25.9 g (0.05 mol) of 1,3,6,8-tetrabromopyrene are then added with stirring to the reaction mixture. The reaction mixture is stirred for 1 hour at room temperature and 24 hours at 40° C. The yellow precipitate is then filtered off with suction, washed with water and methanol and dried for 1 hour at 100° C. in vacuo.

This gives 20 g (=90.5% of theory) of 1,3,6,8-tetraethylmercaptopyrene in the form of an orange-red powder; m.p.: 180° C.

EXAMPLE 4

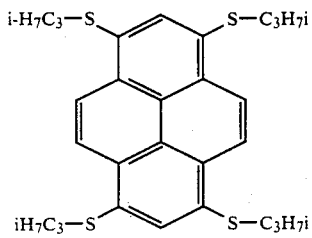

19.6 g (0.2 mol) of sodium isopropyl mercaptide and 26 g (0.05 mol) of 1,3,6,8-tetrabromopyrene are stirred in 200 ml of N,N'-dimethyl-2-imidazolidinone for 5 days at room temperature. The reaction mixture is then introduced into water, and the precipitate is filtered off with suction and recrystallized from ethanol.

This gave 7 g (=28% of theory) of 1,3,6,8-tetraisopropylmercaptopyrene in the form of a yellow crystalline powder; m.p.: 108° C.

EXAMPLE 5

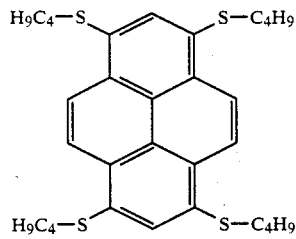

22.4 g (0.2 mol) of sodium butyl mercaptide and 20.7 g (0.04 mol) of 1,3,6,8-tetrabromopyrene are stirred in 250 ml of N,N'-dimethyl 2-imidazolidinone for 1 hour at 80° C. The precipitate is filtered off with suction and washed with water and methanol and dried in a high vacuum.

This gives 17.5 g (=79% of theory) of 1,3,6,8-tetrabutylmercaptopyrene in the form of a yellow fluorescent crystalline powder; m.p.: 91°–92° C.

EXAMPLE 6

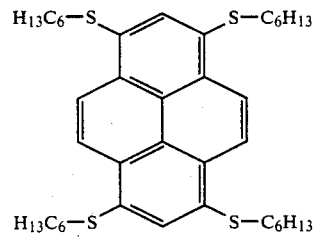

8.4 g (0.06 mol) of sodium hexyl mercaptide and 5.2 g (0.01 mol) of 1,3,6,8-tetrabromopyrene are stirred in 100 ml of N,N'-dimethyl-2-imidazolidinone for 2 hours at 80° C. The precipitate is filtered off with suction and washed with water and methanol and dried in a high vacuum.

This gives 2.5 g (=37% of theory) of 1,3,6,8-tetrahexylmercaptopyrene in the form of a yellow fluorescent crystalline powder; m.p.: 92° C.

EXAMPLE 7

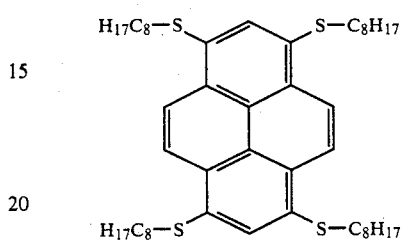

10.2 g (0.06 mol) of sodium octyl mercaptide and 5.2 g (0.01 mol) of 1,3,6,8-tetrabromopyrene are stirred in 100 ml of N,N'-dimethyl-2-imidazolidinone for 1 hour at 80° C. The precipitate is filtered off with suction and washed with water and methanol and dried in a high vacuum. This gives 4.2 g (=53% of theory) of 1,3,6,8-tetraoctylmercaptopyrene in the form of a yellow fluorescent crystalline powder; m.p.: 110° C.

EXAMPLE 8

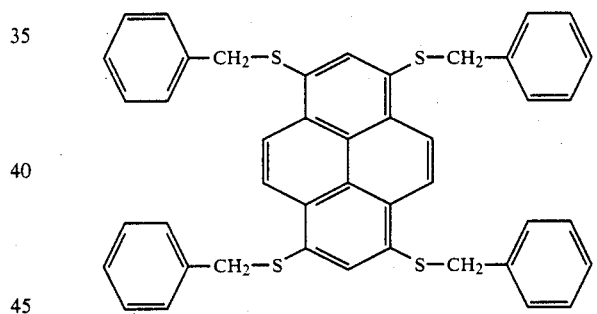

29.4 g (0.2 mol) of sodium benzyl mercaptide and 20.7 g (0.04 mol) of 1,3,6,8-tetrabromopyrene are stirred in 250 ml of N,N'-dimethyl-2-imidazolidinone for 2 hours at 80° C. The precipitate is filtered off with suction and washed with water and methanol and dried in a high vacuum.

This gives 23 g (=83% of theory) of 1,3,6,8-tetrabenzylmercaptopyrene in the form of a yellow fluorescent crystalline powder; m.p.: 178°–180°C.

EXAMPLE 9

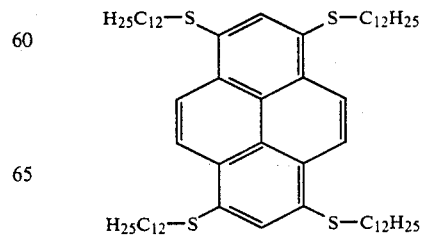

26.9 g (0.12 mol) of sodium dodecyl mercaptide and 13 g (0.025 mol) of 1,3,6,8-tetrabromopyrene are stirred in 500 ml of N,N'-dimethyl 2-imidazolidinone for hours at 80° C. The precipitate is filtered off with suction and washed with water and methanol and dried in a high vacuum.

This gives 15.5 g (=60% of theory) of 1,3,6,8-tetradodecylmercaptopyrene in the form of a yellow fluorescent crystalline powder; m.p.: 110° C.

EXAMPLE 10

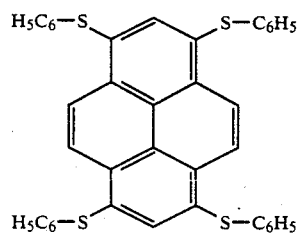

44 g (0.4 mol) of thiophenol are added dropwise with stirring to the solution of 9.2 g (0.4 mole) of sodium in 200 ml of ethanol, which is present in a 500 ml three-necked flask equipped with a stirrer, dropping funnel and reflux condenser. The sodium thiophenolate solution is evaporated to dryness in vacuo, and the residue is suspended in 100 ml of 1,3-dimethyl-2-imidazolidinone. 25.9 g (0.05 mol) of 1,3,6,8-tetrabromopyrene are added to the suspension, the mixture is stirred for 1 hour at room temperature and 24 hours at 40° C. The yellow precipitate is filtered off with suction, washed with water and methanol and dried for 1 hour at 100° C. in vacuo.

This gives 31.5 g (=99.4% of theory) of 1,3,6,8-tetraphenylmercaptopyrene; m.p.: 230° C.

EXAMPLES 11 TO 16

(Preparation of CT complexes of the mercaptopyrenes according to the invention by anodic oxidation)

General Procedure

In an electrolytic cell of 100 ml of capacity equipped with two 16 cm² Pt electrodes (distance between the electrodes: 1 cm), a solution of 1 mmol of tetramethylmercaptopyrene and 5 mmol of conducting salt in 100 ml of nitrobenzene were electrolyzed at a current of 1.5 mA. In the table below, the mercaptopyrene CT complexes obtained, the conducting salts used for the oxidation, the electrolysis time and temperature used and the electric conductivities of the CT complexes (powders) and the yields in which they were obtained are summarized.

TABLE

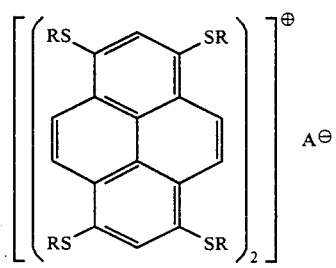

| Examples | R | Conducting salt | A$^\ominus$ | Electrolysis temperature [°C.] | Resulting voltage [V] | Electrol. time [h] | Electric cond. of the CT complex [S/cm] | Yield [% of theory] |
|---|---|---|---|---|---|---|---|---|
| 11 | CH$_3$ | ![quinolinium structure: N-CH$_3$ (+) $^{(-)}$OSO$_2$—OCH$_3$] | CH$_3$OSO$_3^-$ | 80 | 1.4 | 24 | $3.1 \times 10^{-3}$ | 58 |
| 12 | CH$_3$ | [(C$_4$H$_9$)$_4$N]$^+$ClO$_4^-$ | ClO$_4^-$ | 80 | 1.6 | 26 | $4.7 \times 10^{-2}$* | 22.3 |
| 13 | CH$_3$ | [(C$_4$H$_9$)$_4$N]$^+$PF$_6^-$ | PF$_6^-$ | 80 | 1.5 | 26 | $3.7 \times 10^{-2}$ | 34 |
| 14 | CH$_3$ | [(C$_4$H$_9$)$_4$N]$^+$BF$_4^-$ | BF$_4^-$ | 80 | 1.6 | 24 | $2.4 \times 10^{-2}$ | 20.3 |
| 15 | C$_2$H$_5$ | [(C$_4$H$_9$)$_4$N]$^+$PF$_6^-$ | PF$_6^-$ | 20 | 3.7 | 24 | $3.5 \times 10^{-3}$ | 27 |
| 16 | C$_2$H$_5$ | [(C$_4$H$_9$)$_4$N]$^+$BF$_4^-$ | BF$_4^-$ | 20 | 2.4 | 24 | $4.6 \times 10^{-3}$ | 21.7 |

*The conductivity of the crystalline CT complex is, dependent upon the quality of the crystal, 250 to 600 S/cm

EXAMPLE 17

(a) 386 mg (1 mmol) of 1,3,6,8-tetramethylmercaptopyrene and 635 mg (5 mmol) of iodine are heated in 60 ml of 1,2,4-trichlorobenzene to the reflux temperature. After cooling to room temperature, the precipitate is filtered off with suction.

This gives 380 mg (=74.1% of theory) of the CT complex of the formula

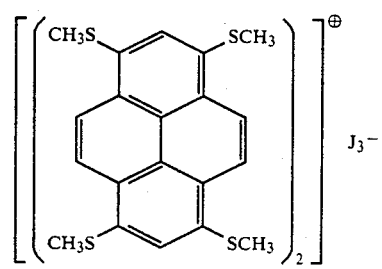

in the form of fine, intertwined black-golden crystalline needles. The electrical conductivity of the CT complex is 8.7 S/cm and its decomposition temperature is 240° C.

(b) (a) is repeated using 1,3,6,8-tetradodecylmercaptopyrene to give the CT complex of the formula

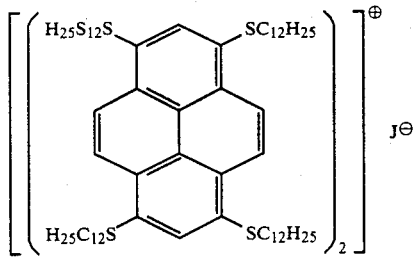

in the form of an olive-green crystalline powder. The electric conductivity of the CT complex is $3 \times 10^{-3}$ S/cm; m.p.: 106°-108° C.

The conductivity of the complex is not impaired by melting.

EXAMPLE 18

(a) A hot solution of 254 mg (2 mmol) of iodine in 10 ml of 1,2,4-trichlorobenzene is added to the hot solution of 772 mg (2 mmol) of 1,3,6,8-tetramethylmercaptopyrene in 10 ml of 1,2,4-trichlorobenzene. Black crystals immediately precipitate out from the reaction mixture. After cooling to room temperature, the precipitate is filtered off with suction and first washed with a small amount of 1,2,4-trichlorobenzene and then with methylene chloride.

This gives 720 mg (=70.2% of theory) of the CT complex of the formula given in Example 13a in the form of black crystals having a golden metallic shine. The electric conductivity of the crystals is 3.2 S/cm.

(b) (a) is repeated using 1,3,6,8-tetraethylmercaptopyrene to give the corresponding CT complex having ethylmercapto groups. The conductivity of this complex is 0.7 S/cm.

EXAMPLE 19

(a) 500 mg (1.3 mmol) of 1,3,6,8-tetramethylmercaptopyrene are stirred at 20° C. into the solution of 164 mg of iodine (1.3 mmol) in 10 ml of methylene chloride. The reaction mixture immediately turns black. After standing for 2 hours at room temperature, the precipitate is filtered off with suction and washed with methylene chloride.

This gives 523 mg (=78.4% of theory) of the CT complex of the formula

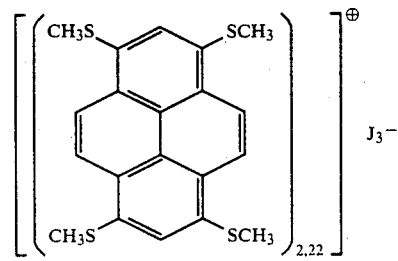

in the form of dark crystals having a golden metallic shine. The electric conductivity of the CT complex is 0.3 S/cm.

(b) (a) is repeated, except that 1,3,6,8-tetrabutylmercaptopyrene is used to give the CT complex of the formula

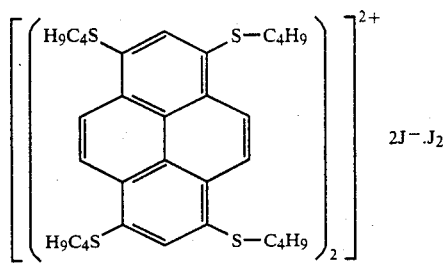

in the form of a black crystalline powder.

The electric conductivity of the CT complex is 0.16 S/cm. The complex melts at 120° C. giving off iodine vapours.

EXAMPLE 20

1 g (1 mmol) of 1,3,6,8-tetradodecylmercaptopyrene and 380 mg (1.5 mmol) of iodine are melted together at 100° C. After cooling, excess iodine is extracted from the melt with methylene chloride. The conductivity of the CT complex thus obtained of the formula given in Example 17b is $5 \times 10^{-3}$ S/cm. Even melting the complex four times does not reduce its conductivity.

EXAMPLE 21

(a) A solution of 0.8 g (5 mmol) of bromine in 10 ml of methylene chloride is added to a suspension of 1.93 g (5 mmol) of 1,3,6,8-tetramethylmercaptopyrene in 40 ml of methylene chloride. After the reaction mixture has been left standing for 2 hours at room temperature, the precipitate is filtered off with suction and washed with methylene chloride.

This gives 2.5 g (=63% of theory) of the CT complex of the formula

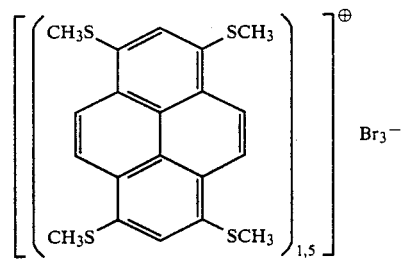

in the form of black crystals. The conductivity of this CT complex is 3.36 S/cm.

(b) (a) is repeated, except that 1,3,6-trimethylmercaptopyrene is used to give the corresponding CT complex having a pyrene substituted by 3 methyl mercapto groups. The conductivity of this CT complex is 1.2 S/cm.

(c) (a) is repeated, except that 1,3,6,8-tetradodecylmercaptopyrene is used to give the corresponding CT complex having a pyrene substituted by 4 dodecylmercapto groups. The conductivity of this CT complex is $3.1 \times 10^{-3}$ S/cm.

EXAMPLE 22

386 mg (1 mmol) of 1,3,6,8-tetramethylmercaptopyrene are added to a solution of 152 mg (1 mmol) of iron(III) chloride (anhydrous) in 10 ml of acetonitrile at 20° C. The reaction mixture quickly turns dark. After stirring for 18 hours at room temperature, the precipitate is filtered off with suction and washed with acetonitrile.

This gives 390 mg (=71.2% of theory) of the charge transfer complex of the formula

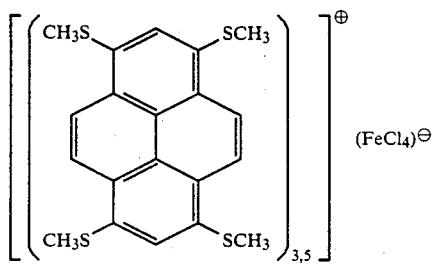

in the form of black crystals. The conductivity of this CT complex is 0.35 S/cm.

EXAMPLE 23

(a) A solution of 3 g (5.2 mmol) of iron(III) tosylate in 10 ml of acetonitrile is added to a solution of 386 mg (1 mmol) of 1,3,6,8-tetramethylmercaptopyrene in 10 ml of acetonitrile. The reaction mixture slowly turns dark. After standing for 12 hours at room temperature, the precipitate is filtered off with suction, washed with acetonitrile and dried.

This gives 0.72 g (=76% of theory) of the CT complex of the composition

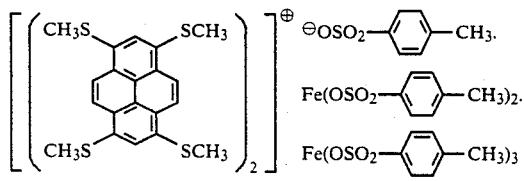

in the form of olive-green crystalline needles. The electric conductivity of these crystals is $7.6 \times 10^{-3}$ S/cm.

(b) (a) is repeated, except that 1.87 g (2 mmol) of iron-(III) 4-dodecylbenzenesulphonate is used as the oxidizing agent to give a CT complex which has a conductivity of $2.3 \times 10^{-3}$ S/cm and melts at 230° C. The conductivity of the complex is virtually unchanged by thermal stress due to melting.

(c) (a) is repeated, except that 1 g (1 mmol) of 1,3,6,8-tetradodecylmercaptopyrene and 0.7 g (1.2 mmol) of iron(III) tosylate are used, to give a yellow-green CT complex whose conductivity is $1.4 \times 10^{-6}$ S/cm.

(d) (a) is repeated, except that 1 g (1 mmol) of 1,3,6,8-tetradodecylmercaptopyrene is used and 1.8 g (1.7 mmol) of iron(III) 4-dodecylbenzenesulphonate is used as the oxidizing agent, to give an olive green CT complex, which admittedly has a conductivity of only $6 \times 10^{-7}$ S/cm but at least has the remarkable property of being deformable under pressure.

EXAMPLE 24

10 drops of $H_2O_2$ (35% strength) are added to a suspension of 193 g (0.5 mmol) of 1,3,6,8-tetramethylmercaptopyrene and 171 mg (0.5 mmol) of tetrabutylammonium perchlorate in 10 ml of tetrahydrofuran. The reaction mixture is subsequently acidified with 10 drops of concentrated sulphuric acid. As a result, it turns black. The precipitate is filtered off with suction, washed with water and methanol and dried.

This gives 152 mg (=70.2% of theory) of the CT complex of the formula

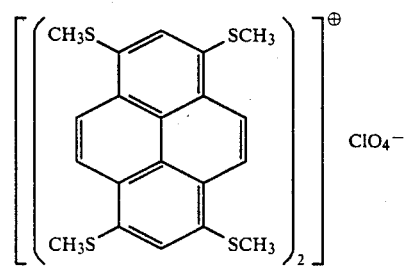

in the form of black crystalline powder. The conductivity of the CT complex is $5.1 \times 10^{-2}$ S/cm; m.p.: 230° C. (with deflagration).

EXAMPLE 25

1 ml of water, 0.3 ml of sulphuric acid (98% strength) and 1 g of tetrabutylammonium perchlorate (3 mmol) are added to a suspension of 772 mg (2 mmol) of 1,3,6,8-tetramethylmercaptopyrene in 1 ml of tetrahydrofuran. A solution of 32 mg (0.2 mmol) of potassium permanganate in 5 ml of water is added to the mixture thus obtained. A black precipitate is formed immediately. This precipitate is filtered off with suction, washed with water and dried.

This gives 0.77 g (=88% of theory) of the CT complex of the formula given in Example 24. The conductivity of the powder is 0.35 S/cm; m.p.: 230° C. (with deflagration).

EXAMPLE 26

Example 24 is repeated, except that instead of $H_2O_2$ 114 mg (0.5 mmol) of ammonium peroxodisulphate are used. This gives 0.205 g (=95% of theory) of the CT complex of the formula

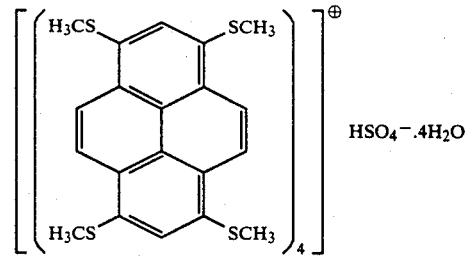

in the form of a black crystalline powder. The conductivity of the CT complex is $1 \times 10^{-2}$ S/cm.

EXAMPLE 27

3 ml of water, 0.3 ml of sulphuric acid (98% strength) and 1 g (6 mmol) of p-toluenesulphonic acid are added to a suspension of 772 mg (5 mmol) of 1,3,6,8-tetramethylmercaptopyrene in 1 ml of tetrahydrofuran. A solution of 32 mg (0.2 mmol) of potassium permanganate in 5 ml of water is then added dropwise to this mixture. The resulting precipitate is filtered off with suction, washed with water and dried.

This gives 0.45 g (=47% of theory) of the CT complex of the formula

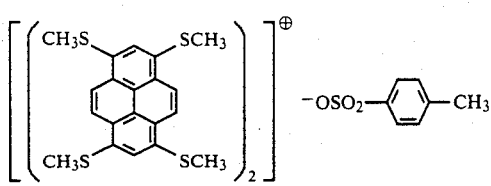
in the form of a black crystalline powder. The electric conductivity of the CT complex is 1.25 S/cm; m.p.: 270° C. (with decomposition).
What is claimed is:
1. The mercaptopyrene of the formula
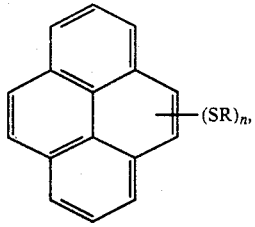
wherein
 n is 4 and
 R is $C_1$–$C_{22}$-alkyl, benzyl or phenyl or $C_1$–$C_{22}$-alkyl, benzyl or phenyl substituted by $C_1$-$C_4$-alkyl, $C_1$-$C_4$-alkoxy or halogen.
* * * * *